United States Patent [19]

Maestrone et al.

[11] Patent Number: 4,839,382

[45] Date of Patent: Jun. 13, 1989

[54] ANTICOCCIDIAL COMPOSITIONS

[75] Inventors: Gianpaolo Maestrone, Staten Island, N.Y.; Eugene G. Schildknecht, Hackettstown; Govind G. Untawale, Wayne, both of N.J.

[73] Assignee: Hoffmann-La Roche Inc., Nutley, N.J.

[21] Appl. No.: 48,169

[22] Filed: May 11, 1987

[51] Int. Cl.$^4$ ............................................. A61K 31/35
[52] U.S. Cl. .................................................. 514/453
[58] Field of Search ................. 514/453; 549/383, 298

[56] References Cited

U.S. PATENT DOCUMENTS

| | | | |
|---|---|---|---|
| 4,199,514 | 4/1980 | Omura et al. | 549/298 |
| 4,218,438 | 8/1980 | Callender et al. | 424/115 |
| 4,366,168 | 12/1982 | Clinton et al. | 514/451 |

FOREIGN PATENT DOCUMENTS 58-88313  5/1983  Japan .................................. 549/298

*Primary Examiner*—Nicky Chan
*Attorney, Agent, or Firm*—Jon S. Saxe; George M. Gould; Dennis P. Tramaloni

[57] ABSTRACT

Compositions comprising a mixture of the antibiotic frenolicin B with one of the ionophorous polyether anticoccidial agents, useful for the treatment and prevention of coccidiosis in animals and methods of treating coccidiosis are disclosed.

17 Claims, No Drawings

ANTICOCCIDIAL COMPOSITIONS

BACKGROUND OF THE INVENTION

The invention relates to the field of compositions useful for the prevention and treatment of coccidiosis in animals, methods of using such compositions and animal comestibles containing such compositions.

Coccidiosis is a disease caused by microscopic protozoal parasites called coccidia, belonging to the genus Eimeria. The infection in the host animals is initiated by the ingestion, usually along with food, water, and/or fecal material, of Eimeria organisms in the sporulated oocyst stage. When the ingested oocysts enter the intestine, the infectious stage of the Eimeria soon develops from the oocysts and causes extensive damage to the inner walls of the intestine and the cecum or "intestinal pouch." Cecal coccidiosis in chickens, for example, is caused primarily by the organism *E. tenella* and results in the destruction of the cecal linings of the host.

Intestinal coccidiosis in chickens results primarily from other species of Eimeria, *E. necatrix, E. acervulina, E. maxima, E. brunetti, E. hagani, E. praecox, E. mitis,* etc. *E. gallopavonis, E. meleagrimitis, E. adenoeides, E. meleagridis, E. dispersa, E. innocua, E. subrotunda,* etc., cause coccidiosis infections in turkeys. In the duck and goose, *E. truncata, E. anseris,* etc., in cattle, *E. bovis, E. zurenii, E. alabamensis, E. auburnensis,* etc., in sheep, *E. ahsata, E. parva, E. faurei, E. arloingi,* etc., in pigs, *E. debliecki, E. spinosa,* etc. cause coccidiosis.

Coccidiosis affects animals such as domestic animals and animals raised commercially for food. Even if such animals survive the infection, serious economic losses still result due to a reduced efficiency in feed utilization and consequent slower growth than normal. Coccidiosis is an especially serious problem in the case of animals raised for food purposes and if not controlled causes serious economic loss in the raising of these animals.

A number of coccidiostatic agents are presently available for the prevention and/or treatment of coccidiosis. Still, many of these agents have certain shortcomings. Animals treated with some of the known coccidiostats sometimes show reduced feed efficiency and lower weight gains than normal. Moreover, the development of resistance to the more commonly used agents is becoming an increasingly significant problem; one which is becoming a limiting factor in successfully combatting coccidiosis. Still other, particularly newer and more potent ionophoric agents, have very narrow safety and efficacy ranges with resulting toxicity risks for treated animals, as well as for other farm animals and man by virtue of incidental or accidental exposure or ingestion.

The most widely used commercially available coccidiostats belong to the group of polyether antibiotics isolated from various strains of bacteria. They are characterized by the cyclic ether moieties in their chemical structures. Examples include monensin, lasalocid, salinomycin, lonomycin and narasin. These antibiotics are also known to those skilled in the art as "ionophores" for what is believed to be their transport-inducing mode of action.

Recently a non-ionophorous antibiotic produced from *Streptomyces roseofulvus,* frenolicin B, has been shown to have some anticoccidial activity against *E. tenella* in chickens (Omura, et al., *J. Antibiotics,* Vol. 38, No. 10, pp. 1447-8 (1985)). Frenolicin B is a naphthoquinone antibiotic having the following structure:

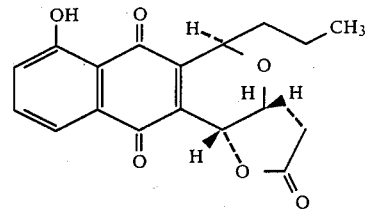

SUMMARY OF THE INVENTION

It has now been discovered that compositions that contain a combination of frenolicin B and an ionophore anticoccidial result in significantly potentiated activity against coccidiosis caused by ionophore resistant Eimeria. The activity of the instant compositions is greater than would be expected from a simple additive effect of the two components.

The present invention, therefore, is directed to compositions which are useful for the prevention and treatment of coccidiosis in animals comprising a mixture of therapeutic amounts of frenolicin B and one of the ionophorous polyether anticoccidial agents. Either or both of these components may optionally be present as the antibiotic or their pharmaceutically acceptable salts or esters as it is well known in the veterinary pharmaceutical art that the ester or salt form of such antibiotics is immaterial in the treatment of an animal and the ester or salt form may be chosen for reasons of economics, convenience, stability and/or toxicity. Furthermore, the present invention is directed to methods for combatting coccidiosis, particularly in poultry, by orally administering the composition disclosed. Finally, this invention relates to animal comestibles containing the composition disclosed.

DETAILED DESCRIPTION OF THE EMBODIMENTS

It has been discovered that compositions containing a polyether anticoccidial agent in combination with frenolicin B are particularly useful for combatting coccidiosis in animals. These compositions are especially useful by virtue of their potentiated activity against particularly virulent ionophore resistant strains of Eimeria and particularly those comprising the coccidiosis producing organisms which affect poultry, such as *E. tenella, E. maxima* and *E. acervulina.*

The compositions of the present invention, when administered to animals such as domestic animals and animals raised commercially for food such as poultry, cattle, sheep and pigs, are effective in the prophylaxis and treatment of coccidiosis. The frenolicin B synergistically interacts with the ionophorous component of the instant composition resulting in greater activity against ionophore resistant coccidiosis. Another advantage of the present invention is that the use of the frenolicin makes possible the use of reduced amounts of the ionophorous component with resulting reduction in the risk of toxicity and the side effects typically associated therewith such as adverse influence on feeding, water intake, and nutrient absorption.

The production and isolation from *Streptomyces roseofulvus* of the frenolicin B utilized in the present invention is disclosed in the article by Iwai et al., *J. Antibiotics,* Vol. 31 No. 10, pp. 959-965 (1978). The polyether component of the present invention may include any of the known anticoccidial ionophores such as, for example, monensin, lasalocid, narasin, nigericin, lonomycin, dianemycin, salinomycin, maduramycin and the trimethylene glycyl ether of maduramycin. Other examples of the class are disclosed in the literature, e.g., in Kirk-Othmer, *Encyclopedia of Chemical Technology*, Vol. 3, 3rd Edition (1978). Still other ionophores useful as coccidiostats are the ethers of maduramycin disclosed in U.S. Pat. No. 4,565,862, monensin urethane derivatives as disclosed in U.S. Pat. No. 4,263,427, and antibiotic X-14934A disclosed in U.S. Pat. No. 4,510,317.

The compositions of the present invention contain as an active ingredient the frenolicin B and the ionophore in the form of the antibiotics or their pharmaceutically acceptable salt or ester. The individual components of the compositions of the present invention are employed in relative amounts which are synergistic in combatting coccidiosis-producing microorganisms and in particular against those strains which have developed resistance or cross-resistance to ionophores due to exposure over time to the latter. The improved anticoccidial animal comestible compositions of this invention are prepared by mixing the active ingredient with suitable carrier or diluent material generally used in animal feeds or drinking water.

The actual concentration of the active ingredient in an animal feed composition of this invention can, of course, be adjusted to the individual needs and may vary over a wide range. The limiting criteria of the concentration are that the minimum concentration is such that a sufficient amount of the active ingredients is provided to effect the desired control of coccidiosis and the maximum concentration is such that the amount of composition ingested does not result in any untoward or undesirable side effects. This may, of course, vary according to the potency and usual recommended dosing level for the particular ionophore selected. Furthermore, because of the potentiating interaction of the active ingredients of the present invention, the amounts of each component required, may usefully be less than that which would ordinarily be considered the usual recommended dosing level for the individual components if used separately as a coccidiostat. The amount of ionophore necessary for successfully combatting coccidiosis may therefor be beneficially reduced. Thus, the ionophore component is typically present in an amount of from about 25 to about 90%, and preferably 33% to 75% of the normal recommended dosing level for that ionophore. For example, an average recommended dosing level for lasalocid in poultry for the prevention of coccidiosis would be about 100 ppm (approved range 75-125 ppm) used hereinafter all references to ppm may be read interchangeably with their equivalent expressed as percentages by weight, i.e., where 1 ppm =0.0001% by weight. The compositions in accordance with the present invention preferably contain the ionophore and frenolicin B in proportions of from about ⅓ to about 3 parts by weight of frenolicin B per part by weight of lasalocid with resulting dosing levels of about 25-30 to about 75-90 ppm of either the lasalocid or frenolicin B based on a typical dosing level for the ionophore.

Other preferred ionophore dose ranges for the present invention in combination with frenolicin B dose levels of 10-100 ppm are:

|  | Feed Dosage | (U.S. FDA Approved Dosage - Poultry) |
| --- | --- | --- |
| Monensin | 30-100 ppm | (99-121 ppm) |
| Salinomycin | 15-50 ppm | (60 ppm) |
| Narasin | 20-50 ppm | (70 ppm) |
| Maduramycin | 2-5 ppm | (N/A) |
| Compound A* | 2-5 ppm | (N/A) |

*trimethylene glycyl ether of maduramycin

The easiest way to administer the antibiotics is by mixing them in the animal's feed. However, the antibiotics can be usefully administered in other ways. For example, they can be incorporated into tablets, drenches, boluses, or capsules, and dosed to the animals. Formulations of the antibiotic compounds in such dosage forms can be accomplished by means of methods well-known in the veterinary pharmaceutical art. Of course, whatever the method or methods of administration, the two antibiotic components of the composition of the present invention can be introduced independently so long as the synergistically effective combination is ultimately dosed to the animal.

The most practical way to treat animals with the antibiotic compounds is by the formulation of the compounds into the feed or drinking water. Any type of feed may be medicated with the antibiotic compounds, including common dry feeds, liquid feeds and pelleted feeds.

The methods of formulating drugs into animal feeds are well-known. It is usual to make a concentrated drug premix as a raw material for medicated feeds. For example, typical drug premixes may contain from about 2.0 to about 150 grams of drug per pound of premix. The wide range results from the wide range of concentration of drug which may be desired in the final feed. Premixes may be either in liquid or dry formulations. Seperately formulated premixes for each of the two components could be added to a given feed lot to provide the composition of the present invention in the final medicated feed.

The formulation of animal feeds containing the proper amounts of antibiotic for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound or of premix, in the feed.

The known methods of formulating, mixing and processing feeds which are normally used in the animal feed arts are entirely appropriate for manufacturing feeds containing the anticoccidial compositions of the present invention. The compositions of the present invention are typically effective in combatting coccidiosis when administered to animals in feed mixes containing the compositions in an amount of from about 0.001% to about 0.025% by weight of the feed mix.

The following examples are illustrative of the invention.

EXAMPLE 1

Anticoccidial Activity Against Ionophore Resistant Field Strains of E. tenella

A composition in accordance with the present invention comprising equal parts of frenolicin B and the ionophore lasalocid was evaluated against two *E. tenella* strains. These strains had been exposed in the field to ionophores, especially monensin, over a long period of time with resulting reduced sensitivity to ionophores as shown by higher mortality and average degrees of infection when tested against recommended dosing levels of several ionophores.

Two-week old broiler chickens, obtained from a commercial hatchery and kept in wire-floored, electrically heated battery brooders, were used in all studies. Ten birds, selected according to weight and sex (50% female and 50% male) were included in each group. The chickens were medicated two days before infection and maintained on the antibiotic until the termination of the trial, six days post-infection. UUC (uninfected, unmedicated controls) and IUC (infected, unmedicated controls) were also included in each study.

Broiler starter mash, a complete feed formula free of drugs, was used as the basal ration. The medicated feed was prepared by adding to the basal ration the desired concentration of drugs. Each drug was thoroughly mixed into the mash prior to use to provide a uniform blend. In all instances, the medicated feed was fed two days before infection and for a total of eight consecutive days.

The infection was induced by giving orally to each bird 1.0 ml of a suspension containing 200,000 sporulated oocysts of *E. tenella*, properly agitated and suspended in sterile distilled water, which was inoculated directly into the crop by means of a blunt needle attached to a calibrated syringe.

At the termination of the trials, the surviving birds were sacrificed, necropsied, and scored for gross lesions. All birds that died during the experiments were also necropsied. Diagnosis was based on lesion location and morphology. The readings obtained were recorded as average degree of infection (ADI) according to the following scoring system: 0=normal, 1=slight, 2=moderate, 3=severe, 4=dead. The ADI was calculated based on the total of individual lesion scores divided by the number of birds scored.

In addition, weight gains (in % relative to UUC) and feed conversion (average feed consumption/average weight gain) were recorded.

The results for the two *E. tenella* strains are shown in Tables 1 and 2. These results show that a 50 ppm +50 ppm dose level of the composition of frenolicin B and lasalocid had significantly greater activity than the 100 ppm dose levels of either lasalocid or frenolicin B alone. This is particularly evident in comparison against the results for 100 ppm of lasalocid. Excellent feed conversion, superior even to the uninfected controls, is also shown.

TABLE 1

| | *E. tenella* Field Isolate FI-276 | | | | |
|---|---|---|---|---|---|
| Treatment | Dosage (ppm) | Weight Gain, % | Feed Conv. | Mort. % | ADI |
| UUC | — | 100 | 1.66 | 0 | 0.0 |
| IUC | — | 48 | 2.55 | 30 | 3.1 |
| Frenolicin B | 100 | 96 | 1.66 | 0 | 0.6 |
| | 80 | 93 | 1.65 | 0 | 0.9 |
| | 60 | 94 | 1.70 | 0 | 1.1 |
| Lasalocid | 100 | 84 | 1.81 | 0 | 2.1 |
| Frenolicin B + Lasalocid | 50 + 50 | 100 | 1.60 | 0 | 0.4 |

TABLE 2

| | *E. tenella* Field Isolate FI-277 | | | | |
|---|---|---|---|---|---|
| Treatment | Dosage (ppm) | Weight Gain, % | Feed Conv. | Mort. % | ADI |
| UUC | — | 100 | 1.76 | 0 | 0.0 |
| IUC | — | 58 | 2.45 | 20 | 3.2 |
| Frenolicin B | 100 | 99 | 1.70 | 0 | 0.7 |
| | 80 | 101 | 1.66 | 0 | 0.7 |
| | 60 | 99 | 1.71 | 0 | 0.8 |
| Lasalocid | 100 | 85 | 2.01 | 0 | 2.2 |
| Frenolicin B + Lasalocid | 50 + 50 | 104 | 1.60 | 0 | 0.2 |

EXAMPLE 2

Anticoccidial Activity Against *E. maxima* Field Isolate

An evaluation in accordance with the method set forth in Example 1 was repeated against a field strain of *E. maxima*, ionophore resistant as a result of exposure to monensin over a long period of time. The results show that a 50+50 ppm dose level of the composition of frenolicin B and lasalocid again showed lower average degre levels of infection than the 100 ppm doses of either frenolicin B or lasalocid used alone. Once again, superior feed conversion was demonstrated for the combination over that for either antibiotic used alone.

| Treatment | Dosage (ppm) | Weight Gain, % | Feed Conv. | ADI |
|---|---|---|---|---|
| UUC | — | 100 | 1.60 | 0.0 |
| IUC | — | 77 | 1.88 | 2.9 |
| Frenolicin B | 100 | 84 | 1.87 | 1.3 |
| | 80 | 81 | 1.85 | 1.5 |
| | 60 | 92 | 1.75 | 1.7 |
| Lasalocid | 100 | 97 | 1.85 | 0.7 |
| Frenolicin B + Lasalocid | 50 + 50 | 95 | 1.62 | 0.5 |

EXAMPLE 3

The procedure of Example I was repeated in an evaluation of anticoccidial activity against an ionophore (monensin) resistant field isolate consisting of a mixture of *E. acervulina* (predominant species) and *E. maxima* with inoculation at 500,000 sporulated oocysts/bird.

| Treatment | Dosage (ppm) | Weight Gain, % | Feed Conv. | ADI |
|---|---|---|---|---|
| UUC | 0 | 100 | 1.69 | 0 |
| IUC | 0 | 72 | 2.14 | 2.8 |
| Frenolicin-B | 50 | 94 | 1.69 | 2.1 |
| Frenolicin-B | 100 | 94 | 1.78 | 1.6 |
| Lasalocid | 50 | 94 | 1.77 | 1.9 |
| Lasalocid | 100 | 95 | 1.66 | 1.2 |
| Lasalocid + Frenolicin-B | 50 + 50 | 97 | 1.66 | 0.5 |
| Lasalocid + Frenolicin-B | 75 + 25 | 95 | 1.67 | 0.6 |
| Lasalocid + Frenolicin-B | 25 + 75 | 90 | 1.83 | 1.5 |
| Lasalocid + Frenolicin-B | 100 + 50 | 94 | 1.73 | 0.3 |
| Lasalocid + Frenolicin-B | 50 + 100 | 96 | 1.67 | 0.7 |

EXAMPLE 4

In order to test the potentiating effect of the frenolicin B composition of the present invention against Eimeria strains exhibiting varying degrees of resistance to various ionophores, the procedure of Example I was repeated against three strains which, graded by resistance to monensin, were respectively highly resistant (TABLE 1), slightly resistant (TABLE 2), ane sensitive (TABLE 3). The three strains and inocula utilized were as follows: TABLE 1—*E.tenella*; 300,000 sporulated oocysts/bird; TABLE 2—*E.maxima*; 200,000 sporulated oocysts/bird; TABLE 3— *E.acervulina*, 500,000 sporulated oocysts/bird. In the results tabulated below, "Compound A" is the trimethylene glycyl ether of maduramycin.

TABLE 1

E. tenella

| Treatment | Dosage (ppm) | Weight Gain % | Feed Conv. | ADI |
|---|---|---|---|---|
| UUC | 0 | 100 | 1.69 | 0.0 |
| IUC | 0 | 68 | 2.47 | 3.1 |
| Frenolicin-B | 50 | 107 | 1.79 | 1.6 |
|  | 30 | 115 | 1.62 | 1.4 |
|  | 10 | 98 | 1.85 | 2.6 |
| Lasalocid | 100 | 100 | 1.76 | 0.9 |
| Lasalocid + Frenolicin-B | 50 + 50 | 99 | 1.80 | 0.3 |
| Lasalocid + Frenolicin-B | 50 + 10 | 99 | 1.83 | 1.3 |
| Monensin | 100 | 59 | 2.73 | 2.5 |
| Monensin + Frenolicin-B | 50 + 50 | 104 | 1.69 | 0.4 |
| Monensin + Frenolicin-B | 50 + 10 | 90 | 2.16 | 1.8 |
| Salinomycin | 60 | 98 | 1.96 | 1.4 |
| Salinomycin + Frenolicin-B | 30 + 30 | 100 | 1.80 | 0.4 |
| Salinomycin + Frenolicin-B | 30 + 10 | 108 | 1.79 | 1.2 |
| Narasin | 70 | 105 | 1.90 | 2.3 |
| Narasin + Frenolicin-B | 35 + 30 | 94 | 1.86 | 1.1 |
| Narasin + Frenolicin-B | 35 + 10 | 92 | 1.92 | 1.4 |
| Maduramycin | 7 | 109 | 1.76 | 0.3 |
| Maduramycin + Frenolicin-B | 4 + 30 | 97 | 1.85 | 0.3 |
| Maduramycin + Frenolicin-B | 4 + 10 | 89 | 1.92 | 0.3 |
| Compound A | 7.5 | 97 | 1.86 | 1.0 |
| Compound A + Frenolicin-B | 4 + 30 | 113 | 1.70 | 0.2 |
| Compound A + Frenolicin-B | 4 + 10 | 108 | 1.77 | 0.7 |

TABLE 2

E. maxima

| Treatment | Dosage (ppm) | Weight Gain % | Feed Conv. | ADI |
|---|---|---|---|---|
| UUC | 0 | 100 | 1.80 | 0.0 |
| IUC | 0 | 73 | 2.27 | 2.5 |
| Frenolicin-B | 50 | 78 | 2.32 | 2.1 |
|  | 30 | 74 | 2.29 | 1.9 |
|  | 10 | 82 | 2.10 | 2.2 |
| Lasalocid | 100 | 97 | 1.96 | 0.6 |
| Lasalocid + Frenolicin-B | 50 + 50 | 98 | 1.94 | 0.1 |
| Lasalocid + Frenolicin-B | 50 + 10 | 103 | 1.79 | 0.8 |
| Monensin | 100 | 97 | 1.95 | 1.4 |
| Monensin + Frenolicin-B | 50 + 50 | 76 | 2.24 | 1.0 |
| Monensin + Frenolicin-B | 50 + 10 | 88 | 2.12 | 1.7 |
| Salinomycin | 60 | 87 | 2.17 | 1.2 |
| Salinomycin + Frenolicin-B | 30 + 30 | 100 | 1.85 | 0.5 |
| Salinomycin + Frenolicin-B | 30 + 10 | 87 | 2.05 | 1.0 |
| Narasin | 70 | 90 | 1.98 | 1.0 |
| Narasin + Frenolicin-B | 35 + 30 | 94 | 1.98 | 0.7 |
| Narasin + Frenolicin-B | 35 + 10 | 88 | 2.08 | 0.8 |
| Maduramycin | 7 | 97 | 2.07 | 0.6 |
| Maduramycin + Frenolicin-B | 4 + 30 | 106 | 1.74 | 0.6 |
| Maduramycin + Frenolicin-B | 4 + 10 | 95 | 1.93 | 0.8 |
| Compound A | 7 | 102 | 1.83 | 0.4 |
| Compound A + Frenolicin-B | 4 + 30 | 89 | 2.08 | 0.6 |
| Compound A + Frenolicin-B | 4 + 10 | 98 | 1.88 | 0.7 |

TABLE 3

E. acervulina

| Treatment | Dosage (ppm) | Weight Gain % | Feed Conv. | ADI |
|---|---|---|---|---|
| UUC | 0 | 100 | 1.71 | 0 |
| IUC | 0 | 76 | 1.96 | 2.9 |
| Frenolicin-B | 50 | 80 | 2.03 | 2.0 |
|  | 30 | 72 | 2.25 | 2.1 |
|  | 10 | 86 | 1.98 | 2.6 |
| Lasalocid | 100 | 104 | 1.67 | 0.2 |
| Lasalocid + Frenolicin-B | 50 + 50 | 104 | 1.66 | 0.6 |
| Lasalocid + Frenolicin B | 50 + 10 | 101 | 1.71 | 0.6 |
| Monensin | 100 | 98 | 2.28 | 0.7 |
| Monensin + Frenolicin-B | 50 + 50 | 94 | 1.77 | 0.8 |
| Monensin + Frenolicin-B | 50 + 10 | 98 | 1.72 | 0.8 |
| Salinomycin | 60 | 93 | 1.79 | 0.2 |
| Salinomycin + Frenolicin-B | 30 + 30 | 101 | 1.73 | 0.6 |
| Salinomycin + Frenolicin-B | 30 + 10 | 96 | 1.80 | 0.5 |
| Narasin | 70 | 90 | 1.77 | 0.3 |
| Narasin + Frenolicin-B | 35 + 30 | 100 | 1.67 | 0.5 |
| Narasin + Frenolicin-B | 35 + 10 | 96 | 1.74 | 0.5 |
| Maduramycin | 7 | 99 | 1.73 | 0.0 |
| Maduramycin + Frenolicin-B | 4 + 30 | 93 | 1.86 | 0.3 |
| Maduramycin + Frenolicin-B | 4 + 10 | 101 | 1.78 | 0.6 |
| Compound A | 7.5 | 103 | 1.66 | 0.1 |
| Compound A + Frenolicin-B | 4 + 30 | 98 | 1.72 | 0.2 |
| Compound A + Frenolicin-B | 4 + 10 | 104 | 1.72 | 0.3 |

We claim:

1. A composition for combatting coccidiosis in animals comprising a first component (a) which is frenolicin B or a pharmaceutically acceptable salt or ester thereof and a second component (b) selected from the group consisting of ionophorous polyether anticoccidial agents and the pharmaceutically acceptable salts and esters thereof wherein each of the said first and second components is present in amounts which in combination are synergistically effective in combatting at least one coccidiosis-causing strain of Eimeria.

2. The composition according to claim 1 wherein (b) is the ionophorous polyether anticoccidial agent selected from the group consisting of lasalocid, monensin, salinomycin, narasin, lonomycin, nigericin, dianemycin, maduramycin, the trimethylene glycyl ether of maduramycin and their pharmaceutically acceptable salts and esters.

3. The composition according to claim 1 wherein (b) is lasalocid, monensin, salinomycin or narasin.

4. A method of combatting coccidiosis in animals which comprises orally administering the composition of claim 1 in an amount sufficient to prevent or treat coccidiosis.

5. A method of claim 4 wherein the composition is orally administered as part of an animal feed wherein the composition comprises from about 0.001% to about 0.025% by weight of the animal feed.

6. A comestible for feeding to animals comprising an animal comestible containing from about 0.001% to about 0.025% by weight of the composition according to claim 1.

7. An animal feed additive premix containing a sufficient amount of the composition according to claim 1 to provide, upon addition of the premix to an animal feed, an animal feed containing from about 0.001% to about 0.025% by weight of said composition.

8. A comestible for feeding to animals comprising an animal feed containing an anticoccidial composition comprising a first component (a) which is the antibiotic frenolicin B or a pharmaceutically acceptable salt or ester thereof in a concentration of about 0.001% to about 0.01% by weight of the animal feed and a second component (b) selected from the group consisting of ionophorous polyether anticoccidial agents and the pharmaceutically acceptable salts and esters thereof in an amount sufficient to be synergistically effective with component (a) in combatting at least one coccidiosis causing strain of Eimeria.

9. The comestible of claim 8 wherein (b) is an ionophorous polyether anticoccidial agent selected from the group consisting of lasalocid, monensin, salinomycin, narasin, lonomycin, nigericin, dianemycin, maduramycin, the trimethylene glycyl ether of maduramycin and their pharmaceutically acceptable salts and esters.

10. The comestible of claim 8 wherein (b) is lasalocid, monensin, salinomycin or narasin.

11. The comestible of claim 8 wherein (b) is lasalocid in a concentration of about 0.0025% to about 0.0090% by weight of the animal feed.

12. The comestible of claim 8 wherein (b) is monensin in a concentration of about 0.0030% to about 0.01% by weight of the animal feed.

13. An animal feed additive premix containing an anticoccidial composition comprising a first component (a) which is the antibiotic frenolicin B or a pharmaceutically acceptable salt or ester thereof and a second component (b) selected from the group consisting of ionophorous polyether anticoccidial agents and the pharmaceutically acceptable salts and esters thereof wherein (a) and (b) are present in an amount sufficient to provide an animal feed containing (a) in a concentration of about 0.001% to about 0.01% by weight of the feed and (b) in a concentration sufficient to be synergistically effective with (a) in combatting at least one coccidiosis-causing strain of Eimeria.

14. The premix of claim 13 wherein (b) is an ionophorous polyether anticoccidial agent selected from the group consisting of lasalocid, monensin, salinomycin, narasin, lonomycin, nigericin, dianemycin, maduramycin, the trimethylene glycyl ether of maduramycin and their pharmaceutically acceptable salts and esters.

15. The premix of claim 13 wherein (b) is lasalocid, monensin, salinomycin or narasin.

16. The premix of claim 13 wherein (b) is lasalocid present in an amount sufficient to provide the lasalocid in a concentration of about 0.0025% to about 0.0090% by weight of the feed.

17. The premix of claim 13 wherein (b) is monensin present in an amount sufficient to provide the monensin in a concentration of about 0.0030% to about 0.01% by weight of the feed.

* * * * *